United States Patent
Dai et al.

(10) Patent No.: US 11,602,432 B2
(45) Date of Patent: Mar. 14, 2023

(54) VALVE CLAMPING DEVICE

(71) Applicant: SHANGHAI HANYU MEDICAL TECHNOLOGY CO., LTD, Shanghai (CN)

(72) Inventors: Yufeng Dai, Shanghai (CN); Huixian Yang, Shanghai (CN); Bingyue Pan, Shanghai (CN); Tao Li, Shanghai (CN)

(73) Assignee: SHANGHAI HANYU MEDICAL TECHNOLOGY CO., LTD, Shanghai (CN)

( * ) Notice: Subject to any disclaimer, the term of this patent is extended or adjusted under 35 U.S.C. 154(b) by 761 days.

(21) Appl. No.: 16/313,139

(22) PCT Filed: Aug. 9, 2018

(86) PCT No.: PCT/CN2018/099618
§ 371 (c)(1),
(2) Date: Dec. 25, 2018

(87) PCT Pub. No.: WO2019/176111
PCT Pub. Date: Apr. 25, 2019

(65) Prior Publication Data
US 2021/0169650 A1    Jun. 10, 2021

(30) Foreign Application Priority Data

Oct. 19, 2017  (CN) .......................... 201710977079.7
Oct. 27, 2017  (CN) .......................... 201711027566.3

(51) Int. Cl.
*A61F 2/24* (2006.01)

(52) U.S. Cl.
CPC .......... *A61F 2/2463* (2013.01); *A61F 2/2466* (2013.01); *A61F 2220/0016* (2013.01);
(Continued)

(58) Field of Classification Search
CPC ........ A61F 2/2463; A61F 2/2466; A61F 2/24; A61F 2/2442; A61F 2/2454; A61F 2/246;
(Continued)

(56) References Cited

U.S. PATENT DOCUMENTS 6,752,813 B2 *  6/2004  Goldfarb ............ A61B 18/1492
                                                  606/139
9,622,863 B2 *  4/2017  Karapetian ........... A61F 2/2436
(Continued)

FOREIGN PATENT DOCUMENTS

CN     102860846 A     1/2013
CN     103826548 A     5/2014
(Continued)

*Primary Examiner* — Yashita Sharma
(74) *Attorney, Agent, or Firm* — Bayramoglu Law Offices LLC (57) ABSTRACT

The present invention discloses a novel valve clamping device and a valve clamping system. The valve clamping device includes a first clamping component, a second clamping component, and a fixing component for fixing the first clamping component and the second clamping component. The first clamping component has at least two first clamping arms. The second clamping component has a corresponding number of second clamping arms. Each of the first clamping arms and the corresponding second clamping arm may be combined into a pair of clamps. The clamping device may adopt designs of a smooth transition at the top, the clamping teeth having high clamping stability, and the fixed ring achieving the purpose of "one thread for two uses".

18 Claims, 6 Drawing Sheets

(52) U.S. Cl.
CPC ............... *A61F 2230/0008* (2013.01); *A61F 2230/0021* (2013.01); *A61F 2230/0054* (2013.01); *A61F 2230/0071* (2013.01)

(58) Field of Classification Search
CPC ...... A61F 2220/0016; A61F 2230/0008; A61F 2230/0054; A61F 2230/0021; A61F 2230/0071; A61F 2220/0041; A61B 17/122; A61B 17/00234; A61B 17/083; A61B 2017/00243; A61B 2017/00783
See application file for complete search history.

(56) References Cited

U.S. PATENT DOCUMENTS

| | | | |
|---|---|---|---|
| 10,603,168 B2 * | 3/2020 | Pan | A61B 17/122 |
| 11,065,119 B2 * | 7/2021 | Abunassar | A61B 17/08 |
| 2002/0013571 A1 | 1/2002 | Goldfarb et al. | |
| 2013/0066341 A1 | 3/2013 | Ketai et al. | |

FOREIGN PATENT DOCUMENTS

| | | |
|---|---|---|
| CN | 103841899 A | 6/2014 |
| CN | 106175986 A | 12/2016 |
| CN | 107019530 A | 8/2017 |
| CN | 107595436 A | 1/2018 |
| CN | 107595437 A | 1/2018 |
| CN | 208808747 U | 5/2019 |
| RU | 2015104885 A | 9/2016 |

\* cited by examiner

VALVE CLAMPING DEVICE

CROSS REFERENCE TO RELATED APPLICATIONS

This application is the national phase entry of International Application No. PCT/CN2018/099618, filed on Aug. 9, 2018, which is based upon and claims priority to Chinese Patent Application No. 201710977079.7, filed on Oct. 19, 2017, and Chinese Patent Application No. 201711027566.3, filed on Oct. 27, 2017, the entire contents of which are incorporated herein by reference.

TECHNICAL FIELD

The present invention relates to a valve clamping device and a valve clamping system, specifically to a valve clamping device and a valve clamping system for treating heart valve regurgitation.

BACKGROUND

Figure 1:
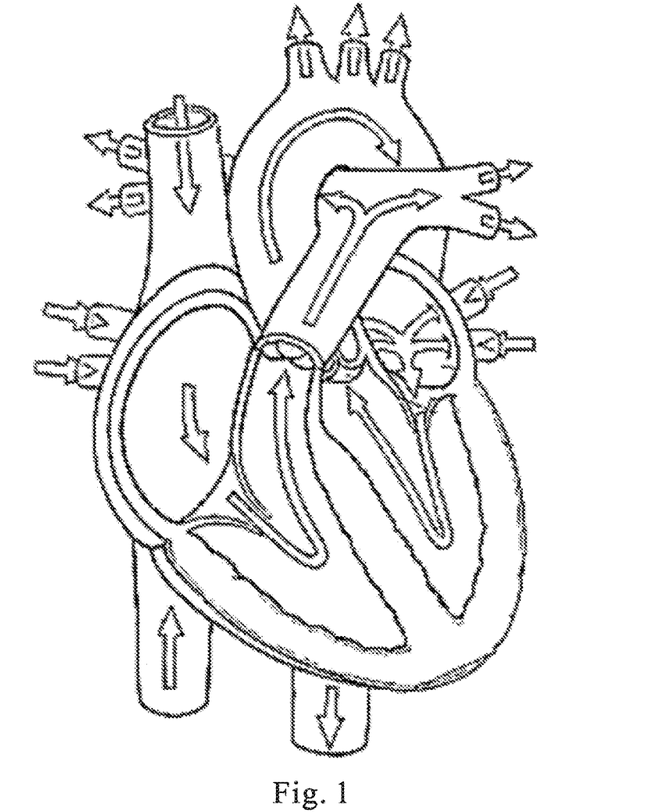
FIG. 1 is a schematic structural diagram of the anatomy of a heart.

The mitral valve is a valve with two flaps attached to the periphery of the left atrioventricular orifice (as shown in FIG. 1), and connected to the papillary muscle by the chordae, which prevents the blood of the left ventricle from flowing back to the left atrium.

Mitral regurgitation (MR) is a series of pathophysiological changes caused by the backflow of blood from the left ventricle to the left atrium, the reason of which is the poor anastomosis of the mitral valve anterior and posterior leaflets caused by the organic or functional changes of the mitral valve leaflets and the related structure thereof. Severe MR may cause enlargement of the left ventricle, eventually leading to left ventricular systolic dysfunction and heart failure, at the same time, left atrial pressure also increases due to the regurgitation, which easily leads to enlargement of the left atrium, atrial fibrillation and pulmonary hypertension. The prognosis of MR is poor, the annual mortality rate of patients with symptoms but without surgery is about 5%, and the 5-year mortality rate of patients with severe heart failure is 60%. Meanwhile, MR is also one of the most common heart diseases. According to statistics, the incidence rates among people over 65 and 75 years old are 6.4% and 9.3%, respectively. With the economic and social development and the population ageing, the incidence rate of mitral regurgitation has increased significantly.

Clinical trials have shown that drug therapy can only improve the patient's symptoms, but not prolong the patient's survival or surgery time. Valve repair or replacement by surgery is considered as the standard treatment for this disease and has been confirmed to be capable of relieving the patient's symptoms and prolonging his life. However, surgery has the disadvantages such as big trauma, obvious postoperative pain, slow recovery, high risk, etc. Moreover, some patients with advanced age, a history of open chest, poor cardiac function and multiple organ dysfunction are often rejected for surgery due to the high risk of surgery. Therefore, the development of minimally invasive, low-risk, MR-treated interventional therapy devices has great social benefits and market needs. In recent years, with the breakthrough of valve interventional therapy technology, MR interventional devices have become one of the key directions of the research and development of cardiovascular devices at home and abroad.

Figure 2A:
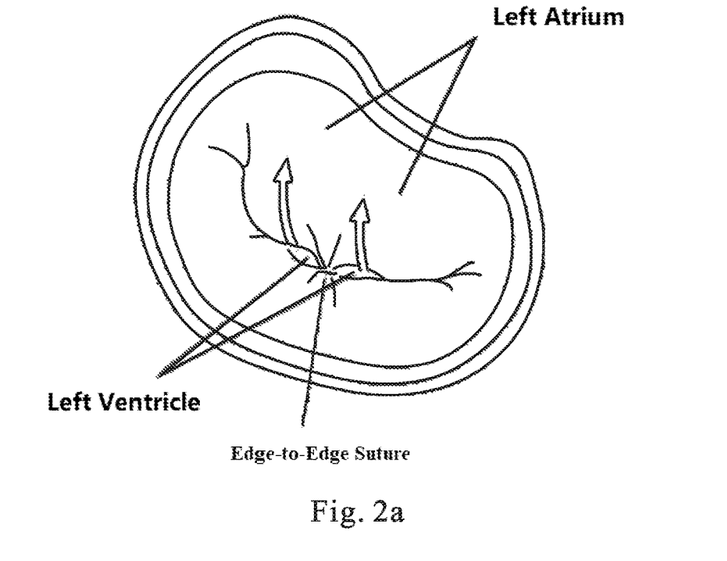
FIG. 2a is a schematic diagram of a surgical mitral valve edge-to-edge suture technique showing the mitral valve in a closed state, and FIG. 2b the schematic diagram of a surgical mitral valve edge-to-edge suture technique showing the mitral valve in an open state.
Figure 2B:
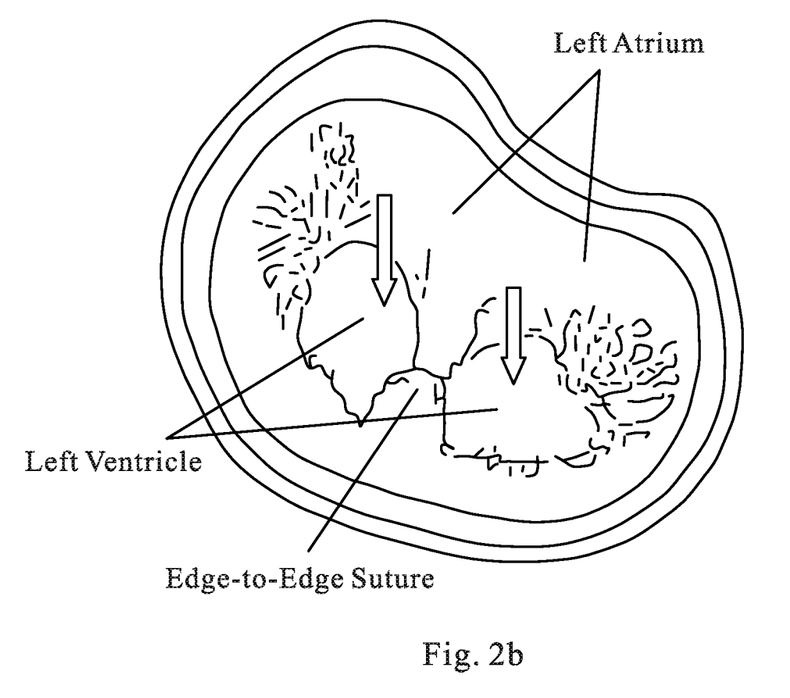

Among them, the valve clamping device developed according to the principle of surgical valve edge-to-edge suture technique is most recognized for its high safety, simple technical principle and great feasibility. The principle of surgical valve edge-to-edge suture technique is as shown in FIG. 2. When the MR occurs, the margins of the two valve leaflets in systolic stage cannot match and close, resulting in a gap through which the blood flows from the left ventricle back to the left atrium. By the surgical edge-to-edge suture technique, the midpoints of the two leaflets of the mitral valve are sutured, so that the gap between the two valve leaflets is changed from one large hole to two small holes during systole, thereby reducing mitral regurgitation (FIG. 2a), and the blood flow flowing into the left ventricle is not affected when the mitral valve is open during diastole (FIG. 2b). The only international minimally invasive interventional device for the treatment of MR receiving market approval is MitraClip provided by Evalve, which is a valve clamping device. However, MitraClip has a complex control system, and the cost of fabrication and production thereof is also high. The device needs to pass through the vein, the right atrium, the interatrial septum, and the left atrium to finally reach the left ventricle during the surgery, the path thereof is long and curved, so the operation of the surgery is very complicated. Surgeons have to repeatedly fine-tune the curvature, direction, horizontal position and vertical depth of the delivery system to reach the ideal position in order to clamp the valve. Therefore, it often takes surgeons a long time to complete a surgery, which is problematic.

CN106175986A discloses a valve clamping device which is simple in both the device structure and operation method. Through the results of the actual production and performance test, it is found that the device still has many defects such as difficulty in capturing the valve, potential damage to the valve, difficulty in enhancing the clamping force, etc.

Therefore, those skilled in the art are focusing on developing a novel valve clamping device and corresponding valve clamping system. On the basis of the traditional version of the clamping device, on one hand, it reduces the damage to the valve during the movement, on the other hand, it facilitates the user to capture the valve and improve the clamping performance, and moreover, it facilitates the production and improves the processability.

SUMMARY

In view of the above-mentioned defects of the prior art, the technical problem to be solved by the present invention is to provide a valve clamping device and a valve clamping system which have more excellent using effect and production realizability.

In order to achieve the above objective, the present invention provides a valve clamping device for treating MR, and the valve clamping device is effective for treating MR after being implanted into a human body by a minimally invasive surgical approach.

The valve clamping device specifically includes a first clamping component, a second clamping component, and a fixing component for fixing the fast clamping component and the second clamping component. The first clamping component has at least two first clamping arms. The second clamping component has a corresponding number of second clamping arms. Each first clamping arm and the corresponding second clamping arm may be combined into a pair of clamps. Distal ends of at least parts of the first clamping arms are outwardly provided with first protrusions and inwardly provided with second protrusions along a clamping direction of the first clamping arms. The first clamping arm and the second clamping arm respectively have a plurality of clamping teeth matched with each other. Preferably, the fixing component is a closed ring.

In a preferred embodiment of the present invention, the distal end of the first clamping arm is configured to have the shape of the end of the femoral head, namely, protrusions are provided along both the clamping direction and the opposite direction, and the distal end of the second clamping arm is also configured as an extending structure having a second extending arm. Therefore, upon completion of the clamping, the positive first protrusion may cooperate with the rounded portion of the tip of the extended second extending arm to realize a tighter clamping. Meanwhile, due to the presence of the reverse second protrusion, the first clamping arm will not continue to move toward the center under the action of the external binding force, thereby limiting the relative position of the distal end of the device. At this point, the second clamping component is continuously clamped by the lantern ring-shaped fixing component, so that the first clamping arm and the second clamping arm are elastically deformed and generate elastic stress against the external binding force. The elastic stress will be transmitted among the components, and makes the device more compact as a whole, so that the clamping performance to the valve is more stable.

Preferably, the distal end of the first clamping component is configured as a curved surface, a plane surface having a rounded transition at a corner, or a combination of the above two having a smooth transition.

Further, the clamping surface of the distal end of the first clamping arm is configured as a fan-shaped surface. In this article, the clamping surface refers to the reverse plane surface of the clamping direction, which is approximately understood to be the contour surface in the side view of the clamping arm.

Further, the setting direction of the clamping teeth of the first clamping arm is inclined toward the proximal end.

Even further, the plurality of clamping teeth of the first clamping arm are discretely arranged along a direction from a proximal end to a distal end of the first clamping arm, and the length of each of the clamping teeth gradually increases along the direction from the proximal end to the distal end.

Further, the fixing component includes a lantern ring region internally provided with a plurality of first fixed teeth, and the second clamping arm has a plurality of second fixed teeth that cooperate with the first fixed teeth. The opening angle of the second clamping component may be changed by changing the depth of the lantern ring region sleeving the second clamping component, and the fixation is achieved by the cooperation of the first fixed teeth and the second fixed teeth.

Even further, the first fixed teeth disposed inside the lantern ring region is an internal thread structure, and the proximal end of the second clamping component is further provided with an external thread matched with the internal thread structure.

Even further, the fixing component substantially has a sleeve structure, and the wall at the proximal end thereof is thinner than the wall at the distal end adjacent thereto. The proximal end of the lantern ring is relatively thin to realize the connection between the fixing component and a conveying tube.

Further, the fixing component is made of polyetheretherketone, high density polyethylene or a combination thereof.

Further, the distal end of the second clamping component is configured into a spherical shape, an ellipsoid shape, a cube shape having a rounded transition or a combination of any two or more above shapes having a smooth transition.

The enumerated limitation to the shape of the distal end of the second clamping component should be understood to mean that the end surface is configured as a three-dimensional image defined by a curved surface that does not contain or substantially does not contain any sharp corners, and further a three-dimensional image defined by curved surfaces such as hyperboloid surfaces, streamlined plane surfaces, etc. and a combination of the three-dimensional images listed above. The streamlined design facilitates smooth movement within the conveying tube without damaging the valve due to the absence of sharp corners, solving the security problem of the conveying and the device.

Further, the second clamping component has a second extending arm, and the second extending arm is at an angle of 110-150 degrees with the second clamping arm and expands outwards. In the present invention, expanding outwards is defined relative to the spindle centerline of the clamping component, that is, expanding outwards means extending along the direction away from the spindle centerline.

Even further, the length of the second extending arm is 3-5 mm.

Further, the second clamping arm has a structure in which the distal end is wide and the proximal end is narrow.

Further, the first clamping arms are at an angle of 115-140 degrees with each other, and the angle between the second clamping arms is 10-30 degrees smaller than the angle between the first clamping arms.

Further, the valve clamping device is made of a material having a high supporting strength, especially an elastic alloy material having strong resilience such as nickel-titanium alloy.

Further, the clamping teeth of the first clamping arm are long sharp teeth, and the clamping teeth of the second clamping arm are short blunt teeth. The clamping teeth of the first clamping arm are sharp and slender, and the clamping teeth of the second clamping arm are short and blunt, since during the surgery, the first clamping arm is located in the atrium, the second clamping arm is located in the ventricle, and there are many chordae on the surface of the ventricle but no chordae on the surface of the atrium. The design is adopted in order to increase the clamping force while avoiding the damage to the chordae inside the ventricle caused by the clamping teeth.

In another aspect, the present invention provides a valve clamping system, including:

a catheter sheath, having a first through hole;

an expanding device, having a second through hole, wherein the second through hole and an outer wall thereof are capable of entering into the first through hole; the second through hole has an inner diameter allowing the penetration of the guide wire; and the axial length of the second through hole is greater than the axial length of the first through hole;

a trans-valve device, wherein the trans-valve device includes a rod body having an outer diameter smaller than an inner diameter of the first through hole and an elastic trans-valve head disposed at one end of the rod body, and the length of the rod body is greater than the axial length of the first through hole;

a conveying device, wherein one end of the conveying device is provided with a conveying tube, the conveying tube has a third through hole, one end of the conveying tube is connected with a closed ring in a detachable manner, and the axial length of the conveying tube is greater than the axial length of the catheter sheath;

a pushing rod, wherein at least a portion of the pushing rod is capable of entering the third through hole, and a length of the portion of the pushing rod capable of entering the third through hole is greater than an axial length of the third through hole;

a loading device, wherein the loading device has a fourth through hole suitable for accommodating at least a portion of the conveying tube, and at least a portion of the outer wall of the fourth through hole is capable of entering into the first through hole; and a first clamping component and a second clamping component, wherein the first clamping component has at least two first clamping arms, and the second clamping component has a corresponding number of second clamping arms; each of the first clamping arms and the corresponding second clamping arm(s) may be combined into a pair of clamps; the first clamping component is adapted to be connected to the distal end of the pushing rod in a detachable manner, the second clamping component is adapted to be connected to the pushing rod in a sliding manner, and the distal end of the closed ring is adapted to be connected to the proximal end of the second clamping component in a detachable manner.

Further, the valve clamping system includes a piercing sheath, and the piercing sheath has a tube section having an inner diameter dimension adapted to accommodate the rod body and the trans-valve head, and an outer diameter dimension adapted to enter the first through-hole.

Further, the conveying device includes a hemostasis valve, preferably a Y-shaped hemostasis valve, and the hemostasis valve is disposed at an end of the conveying device away from the conveying tube.

Further, the expanding device may protrude from the first through hole by 3-8 cm when it completely enters the first through hole.

Further, the transition between a tube body of the expanding device and a tube wall of the catheter sheath is smooth.

Further, the conveying device further includes an operating handle, and the conveying tube and the closed ring are fixed to the operating handle in a silk thread binding manner.

Further, the second clamping component and the pushing rod may relatively slide with a distance of 15-45 mm.

Further, the length of the loading device is 3-15 cm, preferably 5-10 cm, the length of the conveying tube is 35-55 cm, preferably 45-50 cm, and the length of the pushing device is 70-90 cm, preferably 80-85 cm.

Further, the distal end of the closed ring and the proximal end of the second clamping component are respectively provided with an internal thread and an external thread matched with each other, and the second clamping component has fixed teeth that match with the internal thread.

Further, the conveying device includes a storage box configured for the setting of the catheter sheath, the expanding device, the trans-valve device, the conveying device, the loading device, and the pushing rod.

In the present invention, the terms "proximal end" and "distal end" refer to an end judged according to the relative position with the surgical operator in the normal using process during the valve surgery, unless otherwise specified. Wherein, the proximal end refers to an end that is close to the operator, and the distal end refers to an end that is remote from the operator. In the present invention, "inward" refers to the direction close to the centerline of each component, and "outward" refers to the direction away from the centerline of each component. In addition, in the present invention, the first clamping component refers to the upper clamp at the distal end during the surgery, and the second clamping component refers to the lower clamp at the proximal end.

Compared with the prior art, the technical solution of the present invention has the following advantages:

Upon completion of the clamping, the positive first protrusion may cooperate with the rounded portion of the tip of the extended second extending arm to realize a tighter clamping. However, the presence of the reverse second protrusion prevents the first clamping arm from continuing to move toward the center under the action of the external binding force, thereby limiting the relative position of the distal end of the device, so that the components inside the clamping device are more compact during the clamping process, and the clamping performance to the valve is more stable.

The distal end of the first clamping component has a curved structure and does not contain any sharp corners, which facilitates smooth movement within the conveying tube without damaging the valve due to the absence of sharp corners. Therefore, the curved surface design solves the security problems of the conveying and the device at the same time. In addition, the side of the distal end is configured as a fan shape to facilitate the fixation of the valve during the suturing process, and the tectorial membrane is favorable for rapid endothelialization.

The clamping teeth are arranged to be inclined to the proximal end, so that the valve is fixed by the clamping teeth when the valve is captured, avoiding inconvenient operation caused by the valve slippage or the fixation instability. In addition, the size of the clamping teeth gradually increases from the proximal end to the distal end, which may effectively ensure a better fit between the clamping components and a stronger biting force, and improve the clamping stability.

The lantern ring structure is used to fix the clamping components, which may further increase the ability of the clamping arm to clamp the valve tissue, and make the clamped valve tissue move toward the middle. The upper section of the lantern ring structure includes a thread that may be matched with a thread disposed at a proximal end of the second clamping component to fix the second clamping component. In addition, the upper section of the lantern ring structure includes a thread that may be used as the first fixed teeth to match the second fixed tooth in the second clamping portion. The opening angle of the second clamping component may be changed by changing the depth of the lantern ring region sleeving the second clamping component. Thus, the internal thread of the fixing component plays the role of "one thread for two purposes".

The head portion of the second clamping component is configured as an outwardly expanded V shape, and the top is configured as a spherical shape or a shape without sharp corners. The design makes the second clamping component less prone to produce stress concentration points during the process of capturing the valve, and makes the opening angle larger, thereby the valve is easily captured, and at the same time, the design of having no sharp corner makes the damage to the valve smaller. In addition, the second clamping arm is wide at the upper portion and narrow at the lower portion, which facilitates the fixation of the valve during the suturing process.

In addition, in the heart valve clamping system of the present invention, a plurality of components within the system cooperate with each other to perform a series of surgical operations such as catheter sheath delivery, assembly, delivery, and clamping of the valve clamp device, etc. After in vitro assembly, each of the clamping components can be transported to a designated position at one time by the cooperation of the pushing rod and the conveying tube. The second clamping component may slide on the pushing rod, so that the operator may freely adjust the clamping position of the upper and lower clamps before fixing the upper and lower clamps during use, which avoids the problem that the conventional clamping device cannot be repaired once the clamping is mistaken because it cannot be adjusted. The closed ring and the conveying tube are fixed to the operating handle by the wire. After the clamping is completed, the wire may be cut and extracted at the operating handle to separate the conveying tube from the closed ring, and the operation is performed in vitro, which is simple and convenient. The elastic trans-valve head is prepared by using the shape memory alloy, so that the trans-valve head may retract into the tube of the piercing sheath or other components to facilitate conveying during transport.

The concept, the specific structure and the technical effects of the present invention will be further described in conjunction with the accompanying drawings in order to fully understand the objectives, features and effects of the present invention.

List of Reference Numerals: 1—catheter sheath, 2—loading device, 3—expanding device, 4—trans-valve device, 401—trans-valve head, 402—rod body, 5—conveying device, 501—conveying tube, 502—operating handle, 503—Y-shaped hemostasis valve, 6—closed ring, 601—internal thread, 602—conveying tube connection joint, 7—first clamping component, 701—first clamping arm, 702—first clamping tooth, 703—first protrusion, 704—second protrusion, 705—fan-shaped area; 8—second clamping component, 801—second clamping arm, 802—second clamping tooth, 803—dome, 804—second extending arm, 805—external thread, 806—second fixed tooth, and 9—pushing rod.

DETAILED DESCRIPTION OF THE EMBODIMENTS

The present embodiment provides an improved valve clamping device for treating mitral regurgitation, and the valve clamping device discretely includes a first clamping component 7, a second clamping component 8 and a closed ring 6 as a fixing component for fixing the first clamping component 7 and the second clamping component 8 in a detachable manner. Wherein, the first clamping arm 701 and the second clamping arm 801 respectively disposed on the first clamping component 7 and the second clamping component 8 may form a pair of clamps, the first clamping arm 701 and the second clamping arm 801 may be drawn close to each other by an external force to squeeze the valve to achieve the purpose of clamping.

Each functional component in the present embodiment will be described below in detail to better understand the objective and effect of each component design in the present invention.

The valve clamping device in the present embodiment utilizes the clamping arms that cooperate with each other on the clamping components to clamp the valve. In order to improve the clamping ability of the clamping arms to the valve and prevent the clamped valve from slipping, the valve clamping device in the present embodiment is provided with a dentate protrusion at a portion of the clamping arms holding the valve, such as the first clamping teeth 702 on the first clamping component 7 shown in FIG. 3 and the second clamping teeth 802 on the second clamping component 8 shown in FIG. 4 that match the first clamping teeth 702. Wherein, the first clamping teeth 702 are spiny sharp teeth, which can penetrate the valve tissue and enhance the ability of the first clamping teeth 702 to fix the valve. In addition, the spiny structure of the clamping tooth 702 is inclined toward the proximal end, when the first clamping component 7 and the second clamping component 8 cooperate to capture the valve, the valve may be fixed by partially using the spiny structure to prevent the valve from slipping or fixing instability, which reduces the difficulty for the operator to capture the valve. Furthermore, the first clamping teeth 702 on the first clamping component 7 are arranged in such a manner that the size gradually increases in a direction extending from the proximal end to the distal end. Since the opening angle of the second clamping arms 801 of the second clamping component 8 is generally larger than the opening angle of the first clamping arms 701, if all the clamping teeth are configured to have a same length, the clamping teeth of the distal end of the first clamping component 7 cannot be attached to the second clamping arms 801, resulting in unstable clamping. Therefore, the setting mode of the first clamping teeth 702 in the present embodiment may effectively ensure the biting force between the clamping components and improve the stability of the valve clamping. The clamping teeth of the first clamping arms are sharp and slender, and the clamping teeth of the second clamping arms are short and blunt, because during the surgery, the first clamping arms 701 are located in the atrium and the second clamping arms 801 are located in the ventricle, and a plenty of chordae are on the ventricular surface but no chordae is on the atrial surface, in order to increase the clamping force and avoid the damage of the chordae in the ventricle caused by the clamping teeth, the design is adopted. The clamping teeth of the first clamping arms are sharper than the clamping teeth of the second clamping arms.

Figure 3A:
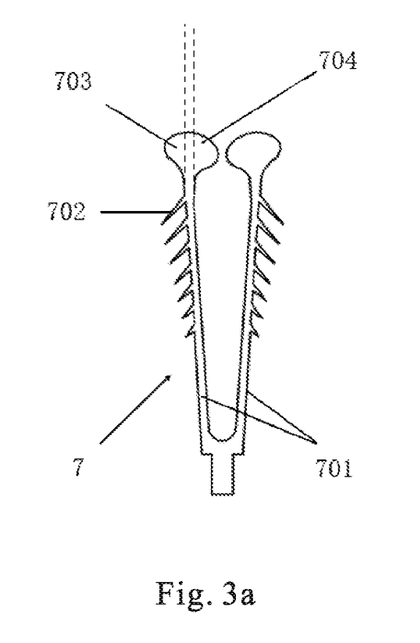
FIG. 3a is a front view of a first clamping component in an embodiment of the present invention.
Figure 3B:
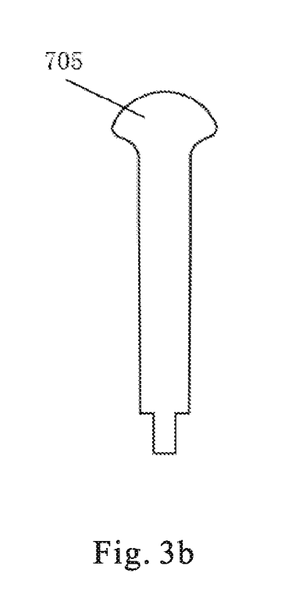
FIG. 3b is a side view of a first clamping component in an embodiment of the present invention.

Another unique design of the valve clamping device in this embodiment is that the head portion of the first clamping component 7 is a structure having a double-sided protrusion shape without sharp corners. Wherein, the protrusion protruding toward the outer side of the clamping device is called the first protrusion 703, the main function of the first protrusion 703 is to cooperate with the ball design at the distal end of the second clamping component 8 to clamp the valve more tightly, achieving a seamless clamping between the upper clamp and the lower clamp. Meanwhile, a second protrusion 704 is further disposed on the other side of the distal end of the first clamping component 7, that is, in the inward direction. The main function of the second protrusion 704 is that when pushing the closed ring to tighten the upper and lower clamps, the second protrusions 704 abut against each other to limit the relative positions of the tops of the second clamping arms, thus the upper and lower clamps may be further tightened only by the bending of the second clamping arms. Since the second clamping arms is supported by a highly elastic alloy such as an iron-nickel alloy, when subjected to the elastic deformation, an elastic stress is generated, thereby generating an internal stress that causes the components of the clamping device to attach to each other closely.

In addition, while designing the first protrusion 703 and the second protrusion 704, the first clamping component 7 also makes the positions where the distal end of the first clamping component 7 contacts the valve and sheath tube free of sharp corners by means of smooth transition of multi-curved surface. In the present embodiment, the top end of the first clamping component 7 is designed as a bionic structure similar to the end of the human femoral head. On one hand, the smooth design ensures that the user may transport the clamping components into the human body more smoothly when using the sheath tube, on the other hand, it ensures that the valve is not damaged due to the absence of sharp corners. Meanwhile, from the side view, the top end of the clamping component is designed as a fan-shaped area 705 on the clamping surface. The structure can utilize the concave structure on both sides of the joint portion and the protrusions on both sides of the top end to better fix the valve during the suturing process, and the and the tectorial membrane performed thereon is favorable for rapid endothelialization.

Figure 4A:
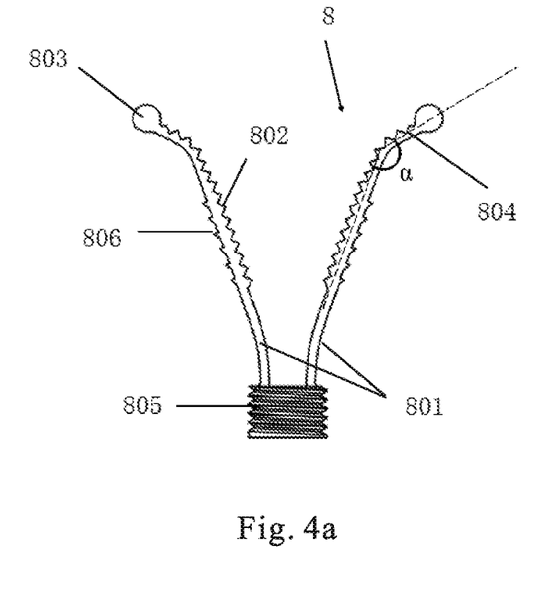
FIG. 4a is a front view of a second clamping component in an embodiment of the present invention.
Figure 4B:
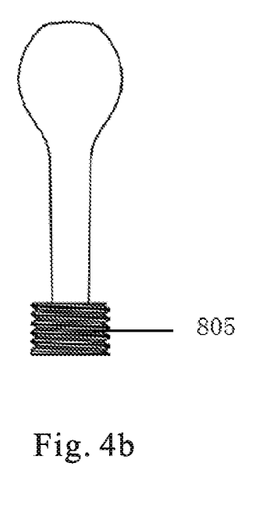
FIG. 4b is a side view of a second clamping component in an embodiment of the present invention.

Similarly, the top end of the second clamping component 8 is also designed with no sharp corners. In the present embodiment, a spherical shape design is adopted to reduce the damage to the valve during the movement. Different from the first clamping component 7, the second clamping component 8 needs to enlarge the top opening angle of the second clamping anus in order to better capture the valve. However, if bent from the bottom of the second clamping arms, the overall clamping arms will incline outwards. When pushing the closed ring 6 to tighten the upper and lower clamps, on one hand, it is difficult for the operator to tighten the upper and lower clamps, on the other hand, it is not conducive to the clamping stability of the top ends of the upper and lower clamps. Therefore, in the present embodiment, the top opening corner of the second clamping arms is increased by bending at the top end of the second clamping arms, or interpreted as by adding an additional second extending arm 804. In the present embodiment, the angle α between the second clamping arm and the second extending arm 804 is about 140 degrees, and the length of the second extending arm 804 is about 3 mm. The design ensures that the second extending arm 804 will not generate stress concentration inside and on the valve during use, thereby ensuring the strength of the second clamping component 8 while reducing the damage to the valve. Moreover, a larger opening angle facilitates the capture of the valve during the surgery and is convenient for operation.

In the present embodiment, as shown in FIG. 3b and FIG. 4b, in order to facilitate the fixation of the valve during the suturing process, the first clamping component 7 and the second clamping component 8 are preferably configured to have a structure with a wide top and a narrow bottom.

Figure 5:
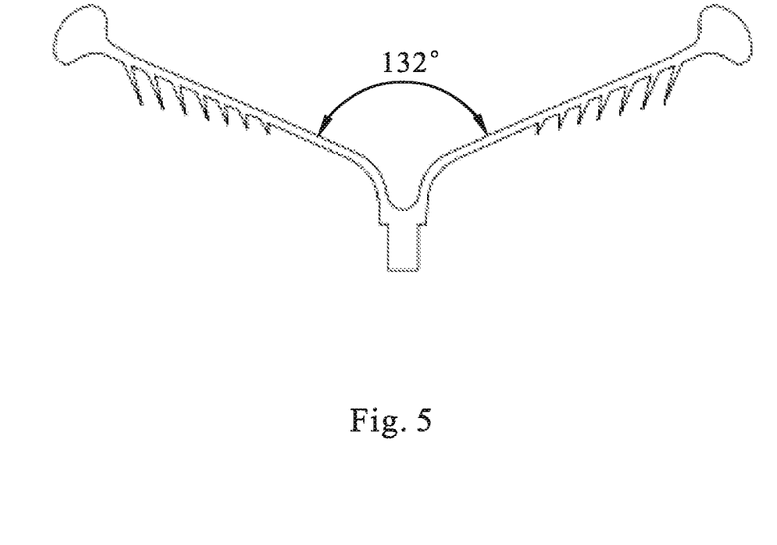
FIG. 5 is a schematic structural diagram of a first clamping component of an embodiment of the present invention.
Figure 6:
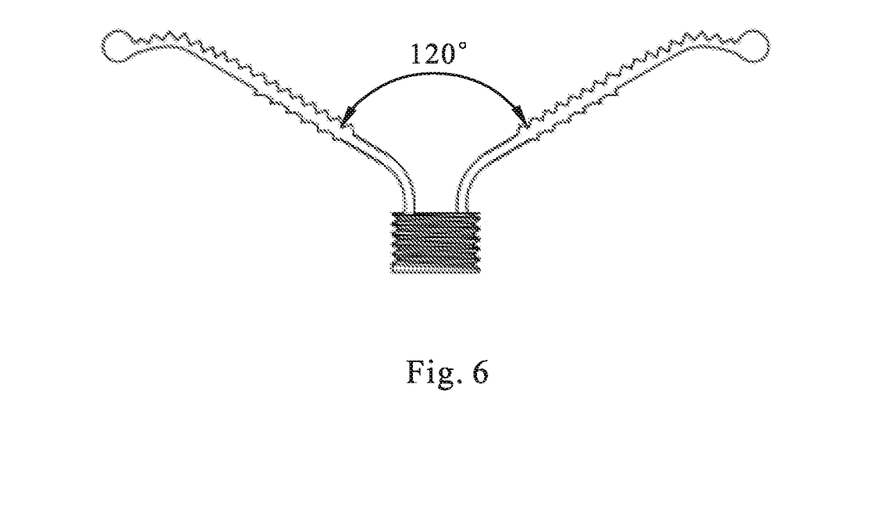
FIG. 6 is a schematic structural diagram of a second clamping component of an embodiment of the present invention.

In the present embodiment, as shown in FIGS. 5 and 6, the first clamping component 7 and the second clamping component 8 are machined, and then shaped by heat treatment (the temperature of the heat treatment process is 400-550° C., and the time is 8-40 min). The first clamping arms of the first clamping component 7 are at an angle of 132 degrees with each other, and the second clamping arms of the second clamping component 8 are at an angle of 120 degrees with each other.

Figure 7:
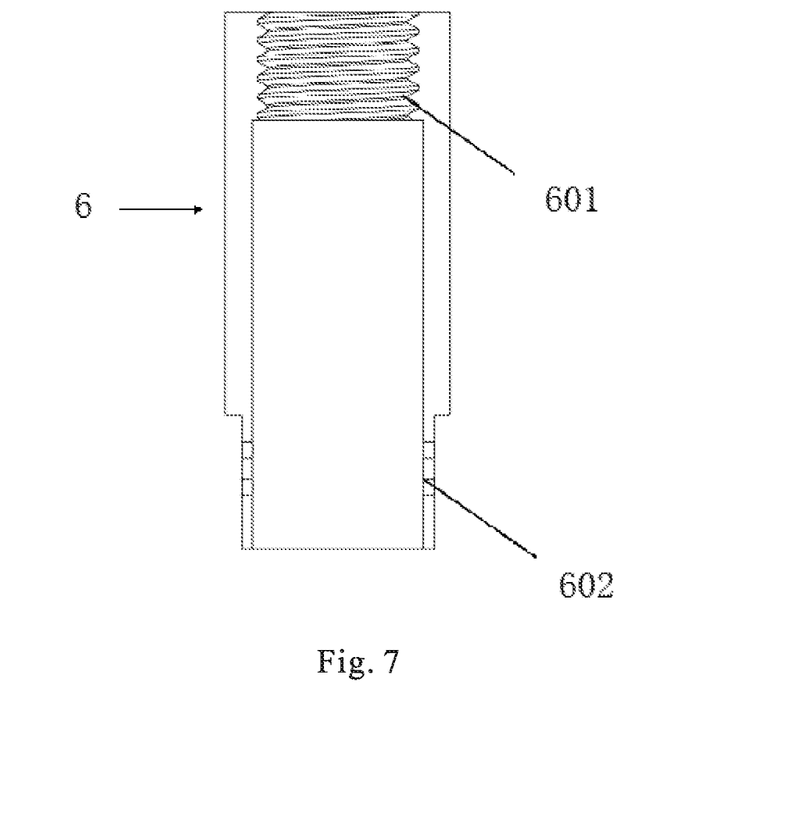
FIG. 7 is a cross-sectional view of a closed ring in an embodiment of the present invention.
Figure 8:
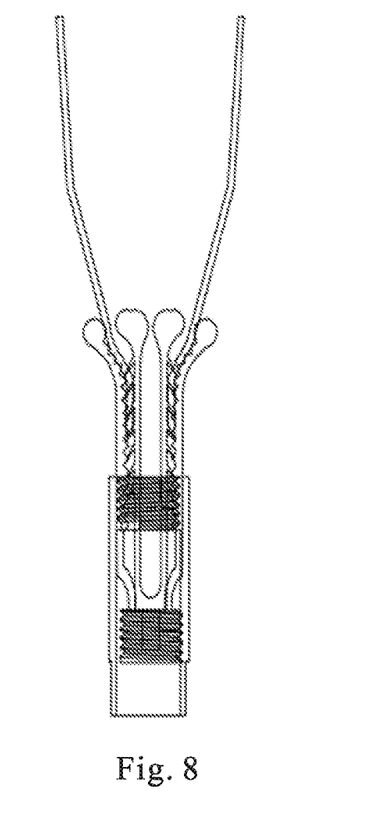
FIG. 8 is a schematic diagram showing a working principle of a valve clamping device in an embodiment of the present invention.

FIGS. 7 and 8 further illustrate the structure of the closed ring 6 in the present embodiment, and how the closed ring 6 cooperates with the first clamping component 7 and the second clamping component 8 to achieve a tight clamping to the valve. As shown in FIG. 7, the clamping device provided in the present embodiment is fixed by a closed ring. The top of the closed ring is a lantern ring structure having an internal thread 601. On one hand, the internal thread 601 may match the external thread 805 at the bottom of the second clamping component 8 to fix the closed ring and the second clamping component 8, on the other hand, it may cooperate with the second fixed teeth 806 on the outer side of the middle portion of the second clamping component 8 to limit the opening angle of the arms of the second clamping component 8. The bottom of the closed ring is thinner and serves as a conveying tube connection joint 602. It should be noted that the second fixed teeth 806 on the outer side of the middle portion of the second clamping component 8 are generally designed to have an anisotropic structure, that is, the proximal end of each fixed tooth adopts an obtuse angle slope shape, so that no jamming occurs when pushing the closed ring, but the distal end adopts a right angle or an acute angle slope shape, so that once the pushing of the closed ring is completed, the fixing between the internal thread 601 and the second fixed teeth 806 will be stable due to the non-slip.

When the second clamping component 8 and the closed ring are transported, the closed ring may be firstly fixed to the second clamping component by the structure of the internal thread 601 and the external thread 805 and then connected to the conveying tube, and the second clamping component 8 and the closed ring are delivered to the distal end of the valve. After the valve is captured, the closed ring is screwed to pass through the threaded section of the second clamping component 8, and the closed ring is further pushed until the internal thread 601 thereof partially coincides with the second fixed teeth 806. At this time, the valve will be pulled toward the center and tightened, and the angle between the clamping components and the clamping force will be adjusted by adjusting the position where the internal thread 601 is inserted into the second clamping component 8, thereby optimizing the clamping state of the valve. As shown in FIG. 8, the stress should be balanced and appropriate in the final valve clamping state, at the top of the valve clamping device, the valve is tightly clamped by using the first protrusion 703 of the first clamping component 7 and the dome 803 of the second clamping component 8, in the middle, the valve is fixed by the spiny clamping teeth of the first clamping part 7, and in the external, the whole clamping device is fixed by the binding force of the closed ring. The whole clamping process is stable and efficient, and the damage to the valve is small.

In the present embodiment, the number of the clamping arms is two sets, in other preferred embodiments, three or more sets of clamping arms may also be used to jointly capture the structure of the valve. It can be understood by those skilled in the art that the number of the clamping arms may be selected according to the actual situation of the patients during the surgery.

Another embodiment of the present invention provides a valve clamping system. The valve clamping system includes an operating component, a delivery component, a functional component and an implanting component, which are all placed in a storage box for easy use during surgery except for the disposable implanting component, wherein: the operating component includes a conveying device 5 and a pushing rod; the delivery component includes a catheter sheath 1, a piercing sheath and a loading device 2; the functional component includes an expanding device 3 and a trans-valve device 4; the first clamping component 7, the second clamping component 8 and the closed ring 6 are the implanting components, which are permanently implanted into the human body after the implantation is completed, so, the three components are usually made of a non-toxic shape memory alloy. Meanwhile, the excellent elasticity thereof may reduce the damage of the components to the organ tissue during the surgery, and clamp the valve more tightly.

The structures and cooperation relationship of various components will be described below in combination with the specific use of each component in the surgery.

During the surgery, how to use the system to deliver the valve clamping device into the human body, complete the clamping action and eventually withdraw the delivery system are described below.

First, the fourth or fifth intercostal space of the left chest of a patient is cut open for 4-6 cm to expose the apex of the heart, and the purse-string suture is performed at the apex. Then, the puncture needle is used to puncture into the left ventricle at the center of the purse string, the guide wire is introduced along the middle hole of the puncture needle, and the puncture needle is pulled out. The puncture needle is a common tool of the operating room, thus does not need to be included in the clamping system.

Figure 9:
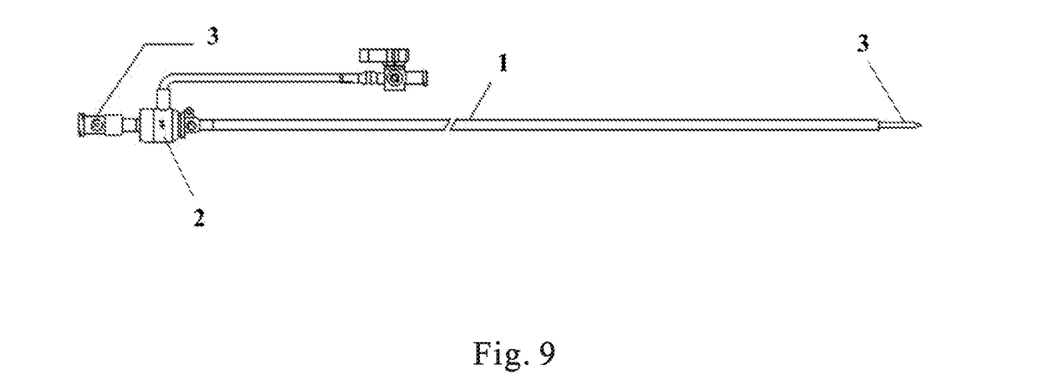
FIG. 9 is a schematic diagram showing structures of a catheter sheath, an expanding device, and a loading device, and a connection relationship thereof in an embodiment of the present invention.

Second, the catheter sheath 1 and the expanding device 3 are introduced along the guide wire. As shown in FIG. 9, the figure shows the connection relationship of the catheter sheath 1, the expanding device 3 and the loading device 2, wherein the catheter sheath 1 is a tubular component and the tube hole thereof is the first through hole. The first through hole may allow the loading tube at the lower right end of the loading device 2 to be inserted therein, and the tube hole of the loading tube is the fourth through hole having an inner diameter sufficient to accommodate several components such as the expanding tube of the expanding device 3, the conveying tube 501 of the conveying device 5, etc. Therefore, during the surgery, the loading device 2 may be used as the proximal end of the delivery component to receive the various operating components and introduce them into the catheter sheath 1 at the distal end.

In the present embodiment, the expanding device 3 and the catheter sheath 1 may be combined together, that is, the expanding device 3 may be inserted into the catheter sheath 1 through the loading device 2. The expanding device 3 has an expanding tube and the tube hole thereof is the second through hole whose inner diameter is adapted to be penetrated by the guide wire. Moreover, viewed from the axial length, the expanding device 3 is longer than the catheter sheath 1, extending about 3-8 cm from the catheter sheath, and the length of catheter sheath 1 is required to be 20-35 cm. The transition between the tube body of the expanding device 3 and the tube wall of the catheter sheath 1 should be smooth, so that the catheter sheath 1 and the expanding device 3 will not scratch the tissue when passing through the myocardium. Once the distal end of the catheter sheath 1 is determined to be already below the horizontal position of the papillary muscle in the ventricle, the expanding device 3, the loading device 2 and the guide wire is pulled out, and catheter sheath 1 is left to be attached to the ventricle.

Figure 10:
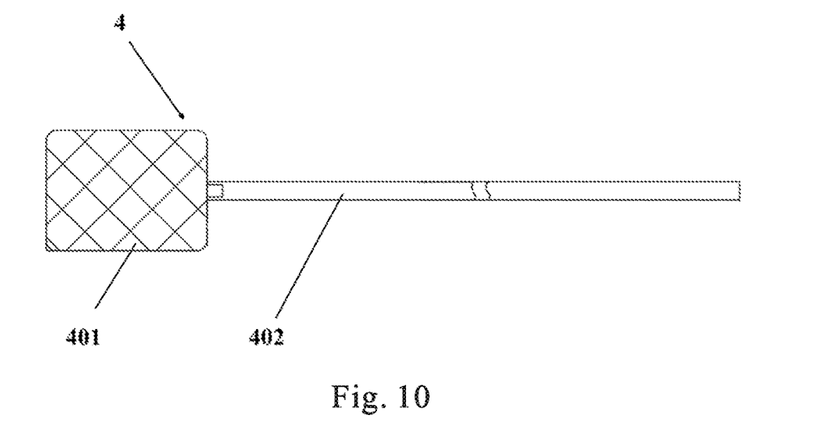
FIG. 10 is a schematic structural diagram of a trans-valve device in an embodiment of the present invention.

Third, in order to achieve the trans-valve step of the distal end of the catheter sheath 1, a trans-valve device 4 is needed to be introduced along the catheter sheath 1. The structure of the trans-valve device 4 is as shown in FIG. 10, and the trans-valve device 4 has a trans-valve head 401 and a rod body 402. The trans-valve head 401 is made of a superelastic nickel-titanium alloy that can be compressed into a 6-8 F piercing sheath (the piercing sheath is a common tool in the operating room, the length is about 10 cm). Since the size of the trans-valve head 401 in the uncontracted state is generally larger than the inner diameter of the piercing sheath, the rod body 402 is first inserted into the piercing sheath during surgery. Since the rod body 402 is about 50-60 cm in length, which is larger than the length of the piercing sheath, when the trans-valve head 401 touches the piercing sheath, the restraining force of the piercing sheath may be used to compress the trans-valve head 401 into the piercing sheath if the rod body 402 is continuously pulled. The piercing sheath is then inserted into the catheter sheath 1 to continue to send the trans-valve device 4 inwards. After the trans-valve ball at the head of the trans-valve device 4 crosses from the anterior and posterior leaflets of the mitral valve and enters the left atrium, the catheter sheath 1 is continued to be sent inward. When the head of the catheter sheath 1 is already in the left atrium, the trans-valve device 4 and the piercing sheath are pulled out.

Figure 11:
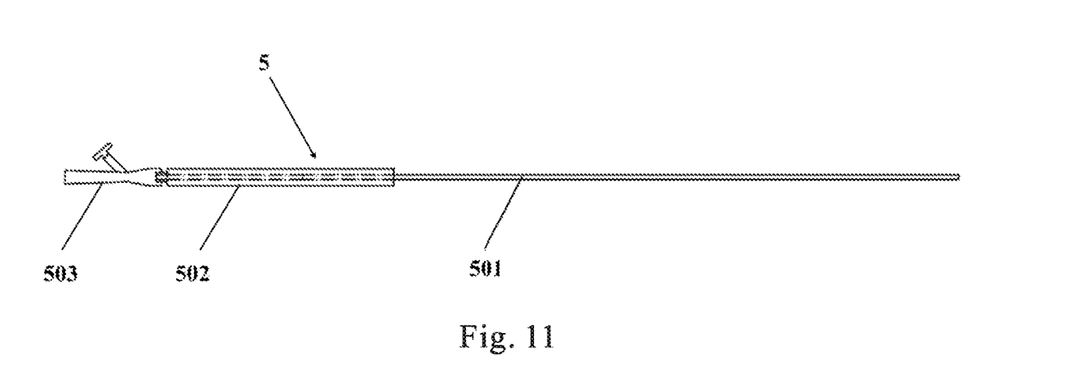
FIG. 11 is a schematic structural diagram of a conveying device in an embodiment of the present invention.

Fourth, in-vitro assembly. The structure of the conveying device 5 is as shown in FIG. 11, and the distal end of the conveying device 5 is a conveying tube 501 and the tube hole thereof is the third through hole. The pushing rod 9 is a rod-shaped component and may enter the third through hole. The loading device 2 has a length of 5-15 cm, the conveying tube 501 has a length of 45-55 cm, and the pushing device has a length of 80-90 cm. A closed ring 6 is mounted at the distal end of the conveying tube 501. The closed ring 6 has a structure as shown in FIG. 6, and the distal end thereof has an internal thread 601. A Y-shaped hemostasis valve 503 is further mounted at the proximal end of the conveying device 5.

Figure 12:
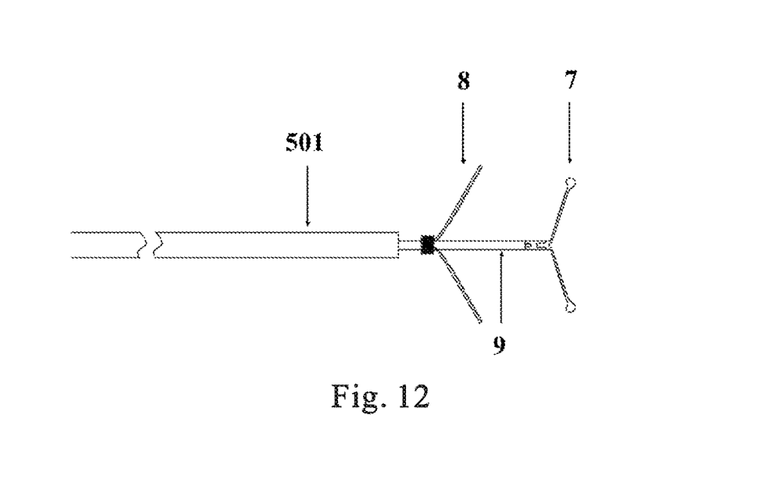
FIG. 12 is a schematic structural diagram showing an in vitro installation of a conveying device, a pushing rod, a first clamping component and a second clamping component in an embodiment of the present invention.

The structures of the first clamping component 7, the second clamping component 8, and the conveying tube 501 after installation are shown in FIG. 12, wherein, the structures of the first clamping component 7 and the second clamping component 8 are respectively shown in FIG. 3a and FIG. 4a. The proximal end of the first clamping component 7 is connected with the pushing rod 9 through thread, the second clamping component 8 is sleeved on the surface of the rod body of the pushing rod 9, and the proximal end of the second clamping component 8 is provided with an external thread 805, which may be matched and connected with the internal thread 601 of the closed ring 6 at the distal end of the conveying tube 501. In addition, the proximal end of the clamping arm of the second clamping component 8 is also provided with clamping teeth, so that the opening angle of the clamping arms of the second clamping component 8 may be further restrained by the internal thread 601 on the closed ring 6 to gather the clamping arms and tightly fix the clamping components.

The in-vitro assembly steps in the surgery are as follows: the conveying tube 501 in the conveying device 5 is inserted into the loading device 2, and then the pushing rod 9 is inserted into the conveying tube 501. There is a hole between the most distal end of the conveying tube 501 and the closed ring 6, the silk thread is passed through the hole for binding, and finally the knot is tied at the operating handle 502. The second clamping component 8 is then put into the pushing rod 9 and slides along the surface of the pushing rod 9 to the bottom. The distal end of the pushing rod 9 is connected with the first clamping component 7 through thread, and the proximal end of the second clamping component 8 is then connected with the distal end of the closed ring 6 through thread to eventually receive the upper and lower clamps into the loading device 2.

Fifth, the loading device 2 is connected with the catheter sheath 1. The operating handle 502 is pushed into the heart until both the first clamping component 7 and the second clamping component 8 are released in the left atrium. The first clamping component 7 and the second clamping component 8 are adjusted to be perpendicular to the on-off direction of the mitral valve, and then the catheter sheath 1 is withdrawn, so that the first clamping component 7 and the second clamping component 8 are respectively on a side of the valve. The first clamping component 7 is pushed up to make the second clamping component 8 capture the valve, and then the first clamping component 7 is pulled down, so that the clamping arms of the first clamping component 7 and the second clamping component 8 clamp the valve. Subsequently, the closed ring 6 is pushed up, so that the left and right clamping arms are gathered into the closed ring 6. The final clamping mode is as shown in FIG. 6.

Sixth, the thread of the pushing rod 9 is screwed off and the pushing device is withdrawn. The knot is cut at the operating handle 502, and the silk thread is withdrawn to separate the conveying tube 501 from the closed ring 6. The conveying device 5, the catheter sheath 1 and the loading device 2 are withdrawn.

Seventh, the purse string is closed, the chest is closed, and then the surgery is completed.

The preferred embodiments of the present invention have been described in detail above. It should be understood that ordinary technicians in the field may make many modifications and changes according to the concept of the present invention without creative work. Therefore, any technical schemes that may be obtained by a person skilled in the art through logical analysis, reasoning or limited experiments on the basis of the prior art in accordance with the concept of the present invention shall be within the protective scope determined by the claims.

What is claimed is:

1. A valve clamping device, comprising:
a first clamping component,
a second clamping component, and
a fixing component for fixing the first clamping component and the second clamping component;
wherein the first clamping component comprises at least two first clamping arms, the second clamping component comprises a same number of second clamping arms corresponding to the at least two first clamping arms, each first clamping arm and one of the second clamping arms corresponding to the first clamping arm are combined into a pair of clamps, a distal end of at least one of the first clamping arms is provided with a head portion having a double-sided protrusion shape without sharp corners, the double-sided protrusion shape outwardly provided with a first protrusion and inwardly provided with a second protrusion along a clamping direction of the one of the first clamping arms, and the first clamping arm and the one of the second clamping arms respectively have a plurality of clamping teeth matched with each other, and
wherein the plurality of clamping teeth of the first clamping arm are discretely arranged along a direction from a proximal end to a distal end of the first clamping arm, and a length of each of the clamping teeth gradually increases along the direction from the proximal end to the distal end of the first clamping arm, and the clamping teeth of the first clamping arm are sharper than the clamping teeth of the second clamping arm;
wherein the fixing component comprises a lantern ring region internally provided with a plurality of first fixed teeth; each second clamping arm comprises a plurality of second fixed teeth matched with the first fixed teeth, wherein the second fixed teeth are on an outer side of a middle portion of the second clamping component.

2. The valve clamping device of claim 1, wherein the fixing component is a closed ring.

3. The valve clamping device of claim 1, wherein a direction of each of the clamping teeth of the first clamping arm is inclined toward a proximal end of the device.

4. The valve clamping device of claim 1, wherein a distal end of the first clamping arm is configured as a curved surface.

5. The valve clamping device of claim 1, wherein a clamping surface of a distal end of the first clamping arm is configured as a fan-shaped surface.

6. The valve clamping device of claim 1, wherein an opening angle of the second clamping component is changed by changing a depth of the lantern ring region with respect to the second clamping component, and a fixation is achieved by a cooperation of the first fixed teeth and the second fixed teeth.

7. The valve clamping device of claim 6, wherein the first fixed teeth disposed inside the lantern ring region is an internal thread structure, and a proximal end of the second clamping component is further provided with an external thread matched with the internal thread structure.

8. The valve clamping device of claim 6, wherein the fixing component is substantially a sleeve structure, and a wall at a proximal end of the fixing component is thinner than a wall at a distal end of the fixing component adjacent to the wall at the proximal end of the fixing component.

9. The valve clamping device of claim 1, wherein a distal end of the second clamping component is configured into a spherical shape, an ellipsoid shape, a cube shape having a rounded transition or a combination of any two or more thereof having a smooth transition.

10. The valve clamping device of claim 1, wherein the second clamping component further comprises a second extending arm, and the second extending arm is at an angle of 110-150 degrees with the second clamping arm and expands outwards.

11. The valve clamping device of claim 1, wherein the second clamping arm has a structure in which a distal end of the second clamping arm is wider than a proximal end of the second clamping arm.

12. The valve clamping device of claim 1, wherein the first clamping arms are at an angle of 115-140 degrees with each other, and an angle between the second clamping arms is 10-30 degrees smaller than the angle between the first clamping arms.

13. A valve clamping system, comprising:
a catheter sheath, having a first through hole;
an expanding device, having a second through hole, wherein the second through hole and an outer wall thereof enter into the first through hole; the second through hole has an inner diameter adapted to be penetrated by a guide wire; and an axial length of the second through hole is greater than an axial length of the first through hole;
a trans-valve device, wherein the trans-valve device comprises a rod body having an outer diameter smaller than an inner diameter of the first through hole and an elastic trans-valve head disposed at one end of the rod body, and a length of the rod body is greater than the axial length of the first through hole;
a conveying device, wherein one end of the conveying device is provided with a conveying tube, the conveying tube comprises a third through hole, one end of the conveying tube is connected with a closed ring in a detachable manner, and an axial length of the conveying tube is greater than an axial length of the catheter sheath;
a pushing rod, wherein at least a portion of the pushing rod enters the third through hole, and a length of a rod section of the pushing rod entering the third through hole is greater than an axial length of the third through hole;
a loading device, wherein the loading device comprises a fourth through hole adapted to accommodate at least a portion of the conveying tube, and at least a portion of an outer wall of the fourth through hole enters into the first through hole; and
a first clamping component and a second clamping component, wherein the first clamping component comprises at least two first clamping arms, and the second clamping component comprises a same number of second clamping arms corresponding to the at least two first clamping arms; each first clamping arm and one of second clamping arms corresponding to the first clamping arm are combined into a pair of clamps; a distal end of at least one of the first clamping arms is provided with a head portion having a double-sided protrusion shape without sharp corners, the double-sided protrusion shape outwardly provided with a first protrusion and inwardly provided with a second protrusion along a clamping direction of the one of the first clamping arms, and the first clamping arms and the one of the second clamping arms respectively have a plurality of clamping teeth matched with each other, and the plurality of clamping teeth of the first clamping arm are discretely arranged along a direction from a proximal end to a distal end of the first clamping arm, and a length of each of the clamping teeth gradually increases along the direction from the proximal end to the distal end of the first clamping arm, and the clamping teeth of the first clamping arm are sharper than the clamping teeth of the second clamping arm, the first clamping component is adapted to be connected to a distal end of the pushing rod in a detachable manner, the second clamping component is adapted to be connected to the pushing rod in a sliding manner, and a distal end of the closed ring is adapted to be connected to a proximal end of the second clamping component in a detachable manner;
a fixing component for fixing the first clamping component and the second clamping component, wherein the fixing component comprises a lantern ring region internally provided with a plurality of first fixed teeth; each second clamping arm comprises a plurality of second fixed teeth matched with the first fixed teeth, wherein the second fixed teeth are on an outer side of a middle portion of the second clamping component.

14. The valve clamping system of claim 13, wherein the valve clamping system further comprises a piercing sheath, and the piercing sheath comprises a tube section having an inner diameter dimension adapted to accommodate the rod body and the elastic trans-valve head, and an outer diameter dimension adapted to enter the first through-hole.

15. The valve clamping system of claim 13, wherein the conveying device further comprises a hemostasis valve disposed at an end of the conveying device away from the conveying tube.

16. The valve clamping system of claim 13, wherein a transition between a tube body of the expanding device and a tube wall of the catheter sheath is smooth.

17. The valve clamping system of claim 13, wherein the conveying device further comprises an operating handle, and the conveying tube and the closed ring are fixed to the operating handle in a silk thread binding manner.

18. The valve clamping system of claim 13, wherein a distal end of the closed ring and a proximal end of the second clamping component are respectively provided with an internal thread and an external thread matched with each other, and the second clamping component comprises fixed teeth that cooperate with the internal thread.

* * * * *